United States Patent [19]

Dibie et al.

[11] Patent Number: 5,531,788
[45] Date of Patent: Jul. 2, 1996

[54] ANTI-PULMONARY EMBOLISM FILTER

[75] Inventors: Alain Dibie, Paris; Dominique Musset, Rueil, both of France

[73] Assignees: Foundation pour l'Avenir pour la Recherche Medicale Appliquee, Paris; Association pour la Recherche en Imagerie de l'Hopital Antoine Beclere, Clamart, both of France

[21] Appl. No.: 239,831

[22] Filed: May 2, 1994

Related U.S. Application Data

[63] Continuation of Ser. No. 844,617, Apr. 9, 1992, abandoned.

[30] Foreign Application Priority Data

Dec. 14, 1989 [FR] France .................. 89 16538
Oct. 9, 1990 [FR] France .................. 89 13160

[51] Int. Cl.⁶ .................. A61F 2/02; A61B 17/08; A61M 29/00
[52] U.S. Cl. .................. 623/11; 606/158; 606/200
[58] Field of Search .................. 623/1, 4; 128/833, 128/DIG. 22; 606/194, 200, 157, 158

[56] References Cited

U.S. PATENT DOCUMENTS

| | | | |
|---|---|---|---|
| 4,756,711 | 7/1988 | Mai et al. .................. | 623/23 |
| 4,873,978 | 10/1989 | Ginsburg .................. | 606/200 |
| 4,957,501 | 9/1990 | Lahille et al. .................. | 606/200 |
| 4,994,069 | 2/1991 | Ritchart et al. .................. | 623/11 |
| 5,152,777 | 10/1992 | Goldberg et al. .................. | 606/200 |

FOREIGN PATENT DOCUMENTS

| | | | |
|---|---|---|---|
| 0121447 | 10/1984 | European Pat. Off. . | |
| 0293605 | 12/1988 | European Pat. Off. .................. | 623/11 |
| 0323333 | 7/1989 | European Pat. Off. . | |
| 0348295 | 12/1989 | European Pat. Off. .................. | 623/11 |
| 2616666 | 12/1988 | France . | |
| 3203410 | 11/1982 | Germany .................. | 623/1 |

Primary Examiner—Debra S. Brittingham
Attorney, Agent, or Firm—Jacobson, Price, Holman & Stern

[57] ABSTRACT

The present invention relates to an anti-pulmonary embolism filter of the type made of a remanent spring effect resilient wire, characterized in that it is shaped into a spiral (1) having three non-touching turns (2, 3, 4) with the middle turn (3) having a diameter (d3) greater than the diameters (d2, d4) of the other two turns, and in that this diameter (d3) is selected to be close to the half-circumference of the vena cava in the zone where the filter is to be implanted so as to ensure that the function of holding the filter in place by flattening of the vena cava is optimized.

27 Claims, 8 Drawing Sheets

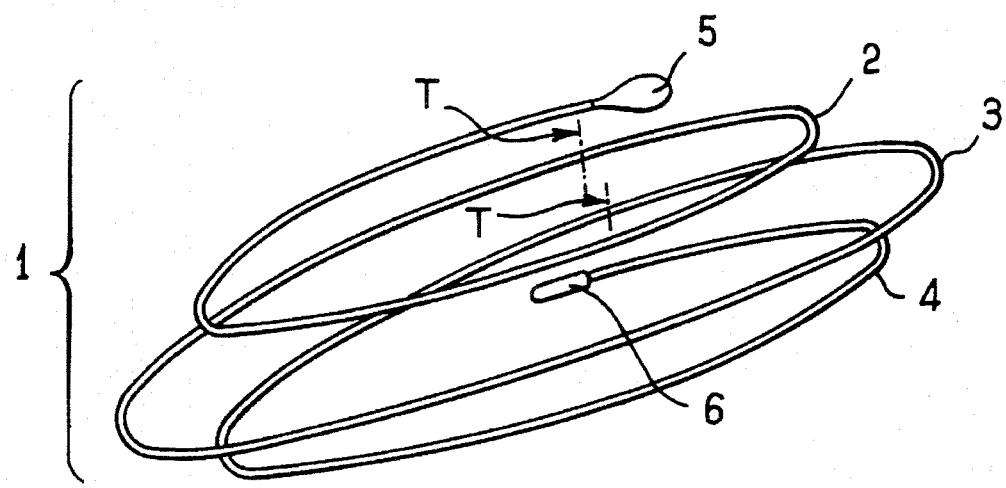
FIG_1
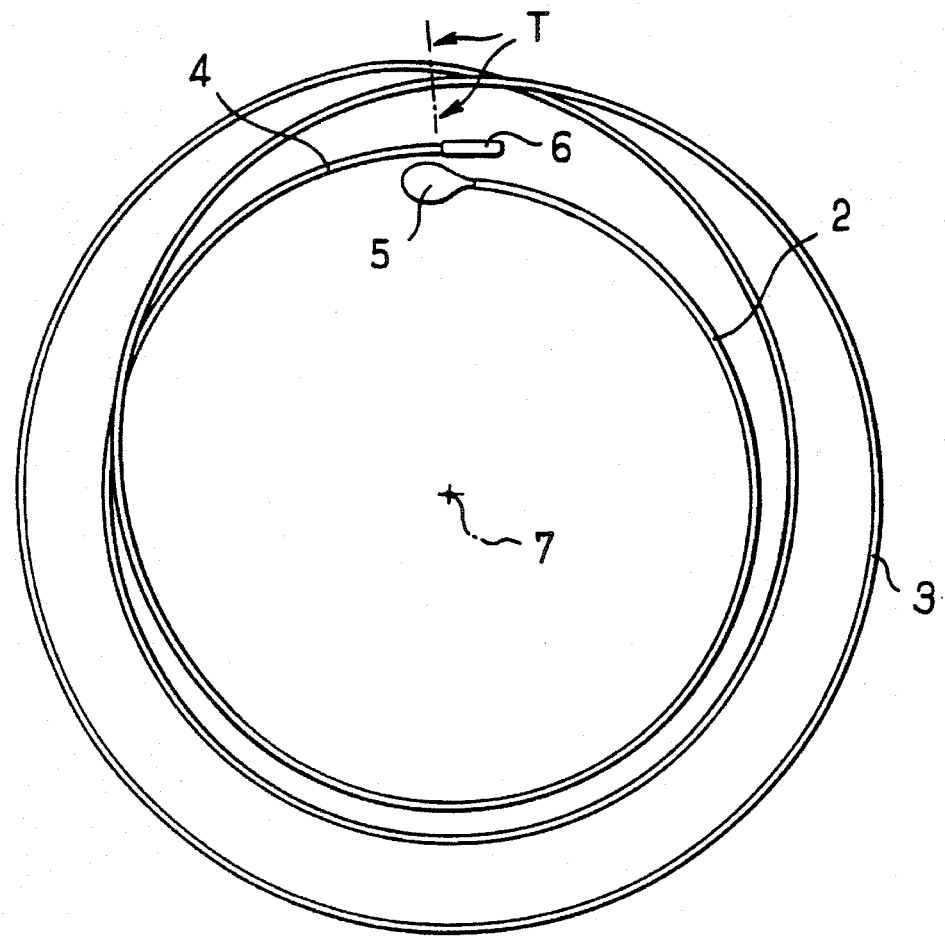
FIG_2

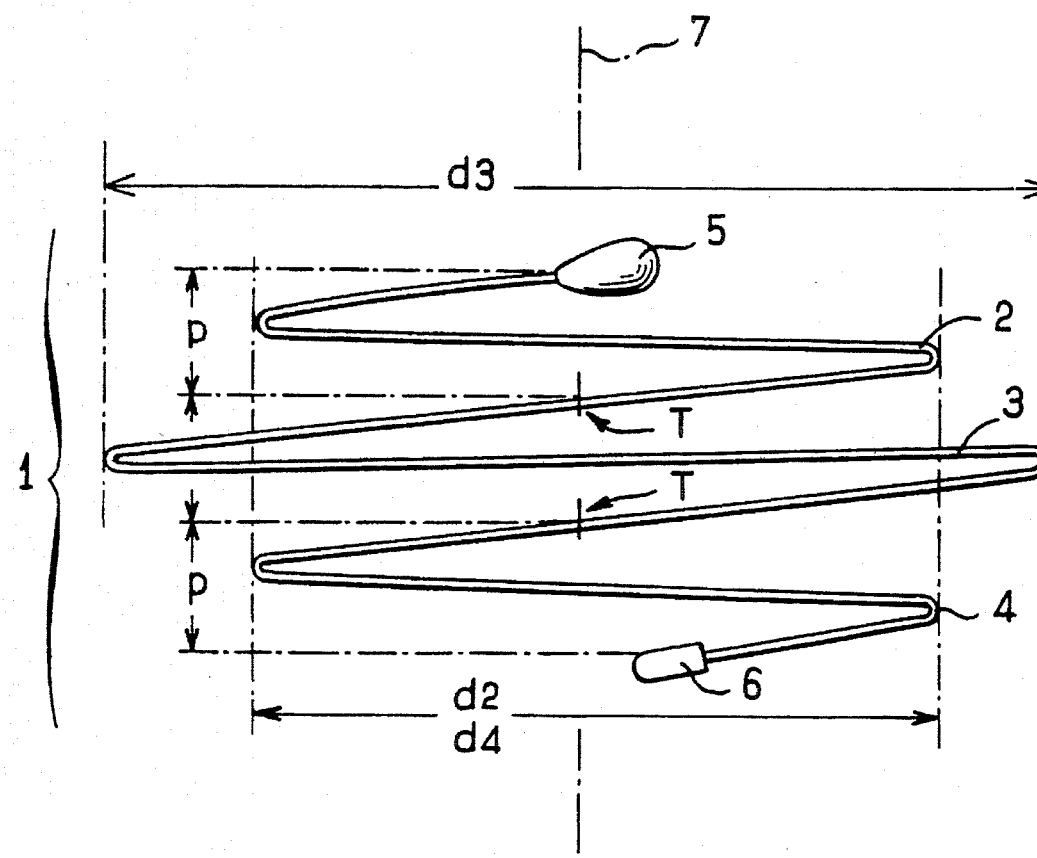
FIG_3
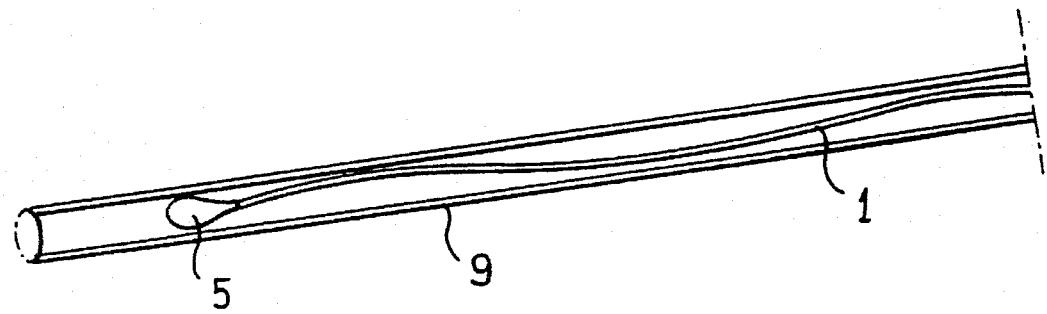
FIG_4

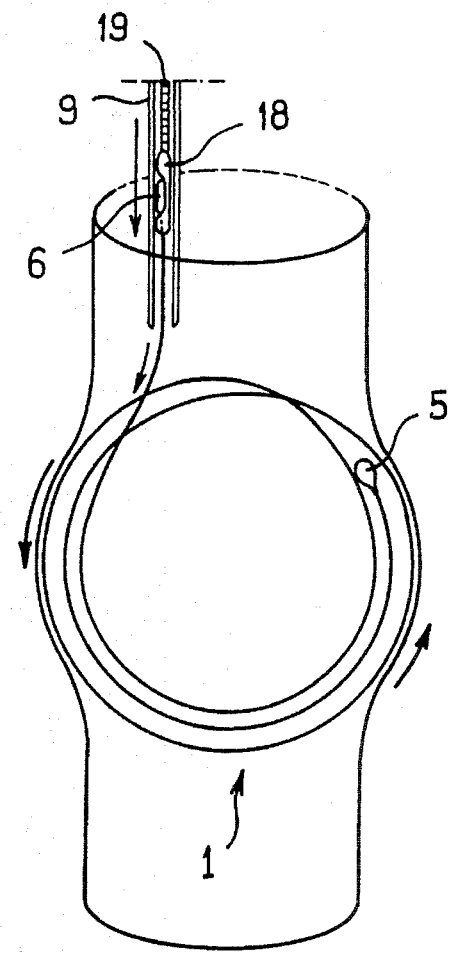
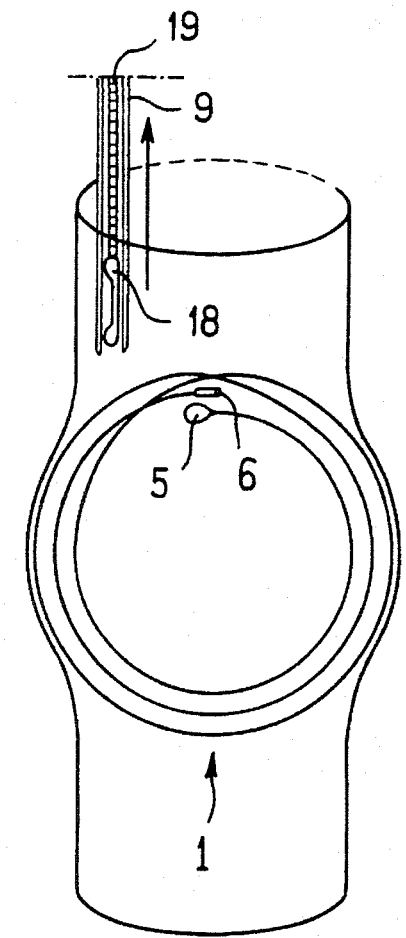
FIG.5  FIG.6
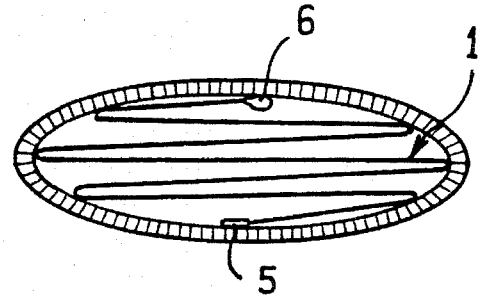
FIG.7
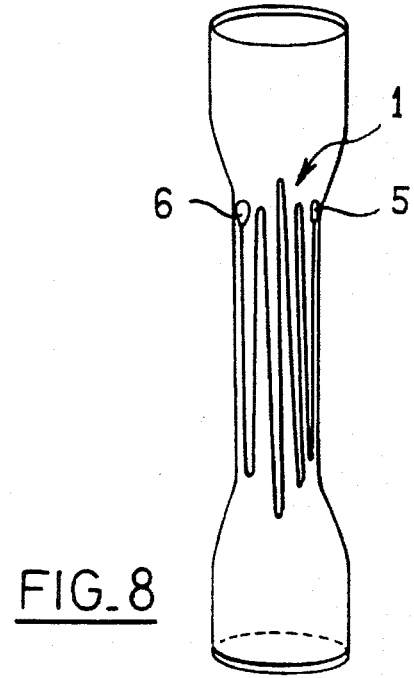
FIG.8

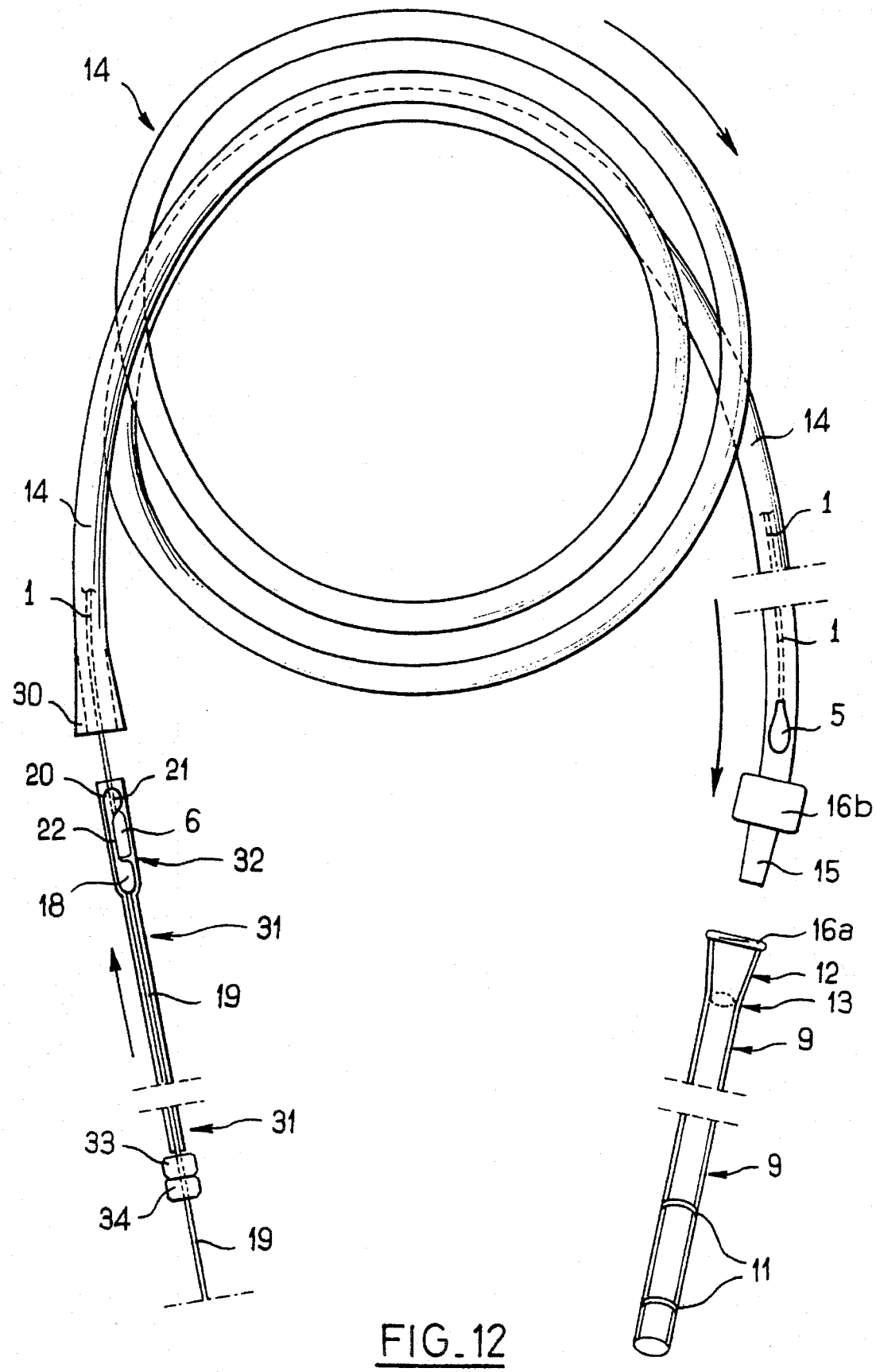
FIG_12

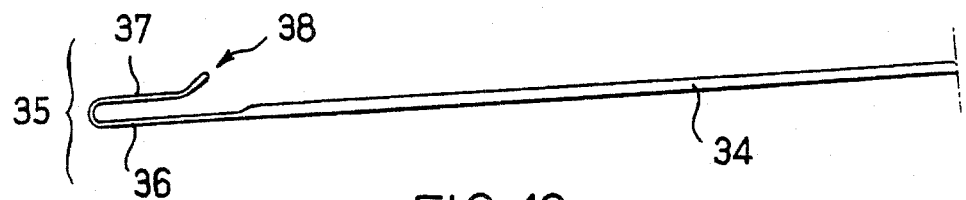
FIG_13
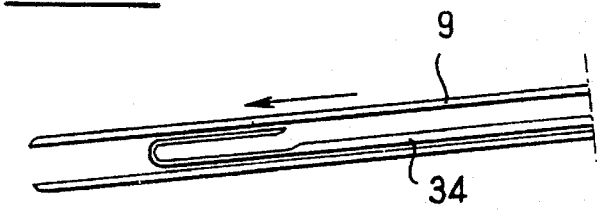
FIG_14
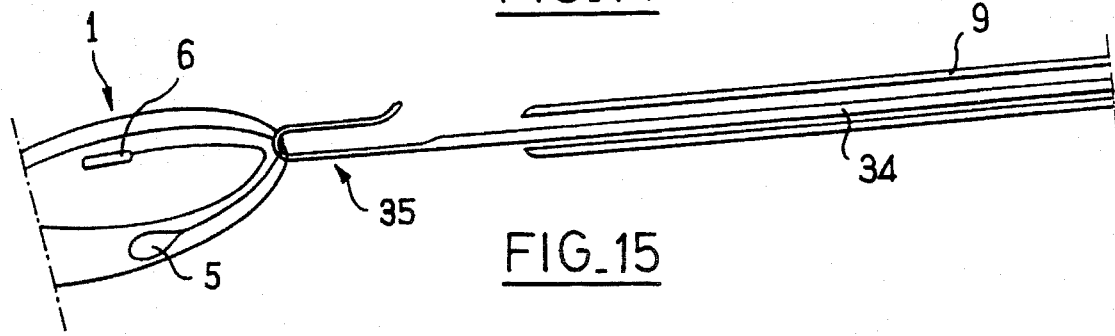
FIG_15
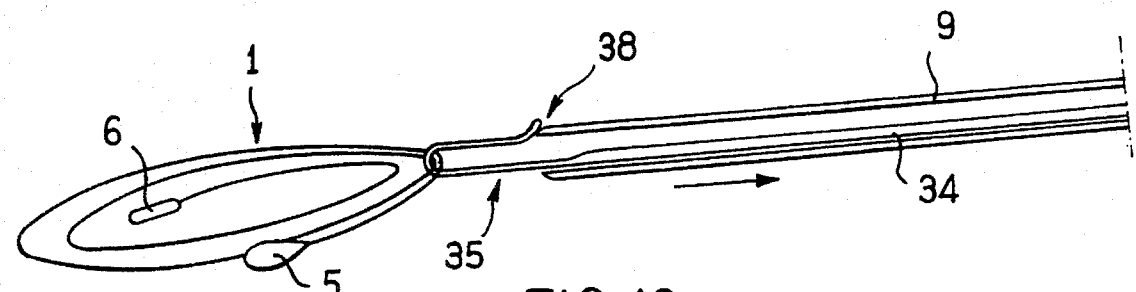
FIG_16
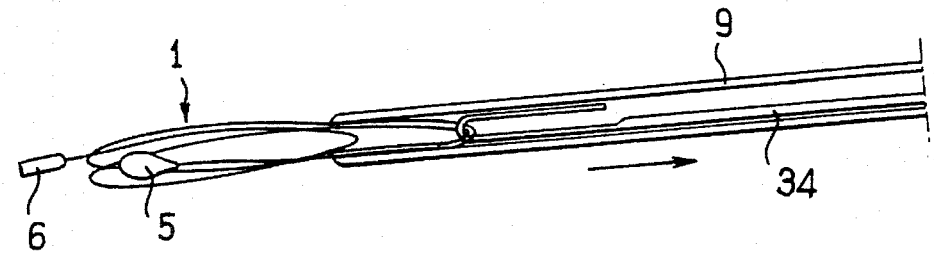
FIG_17

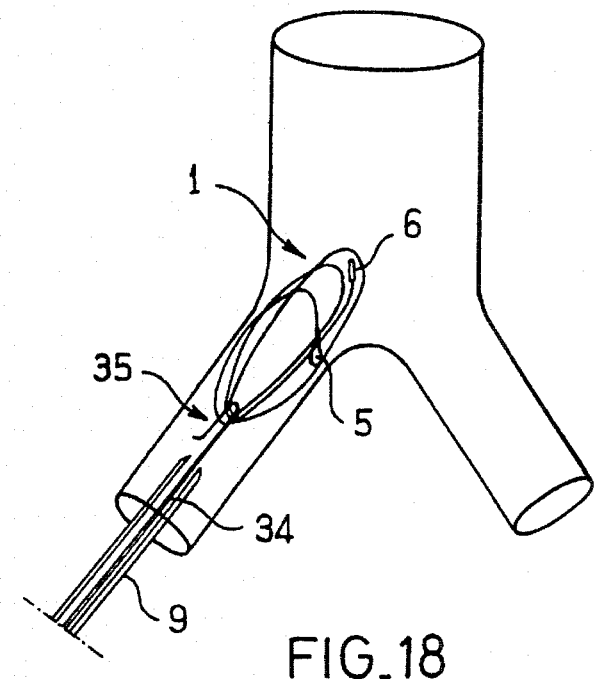
FIG_18
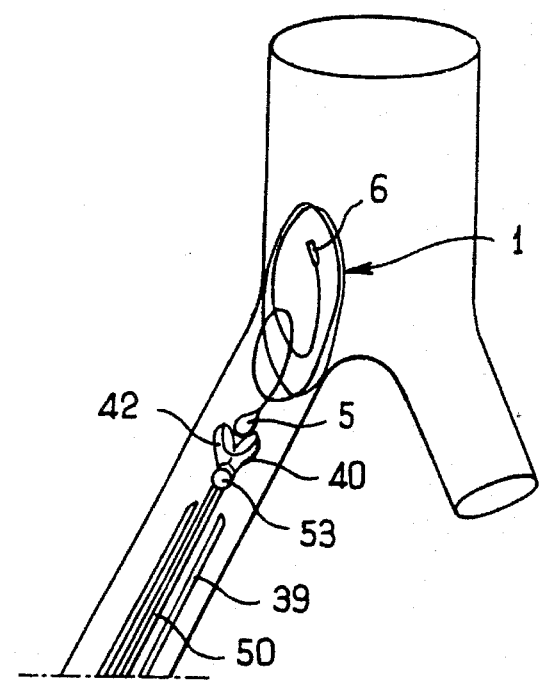
FIG_19
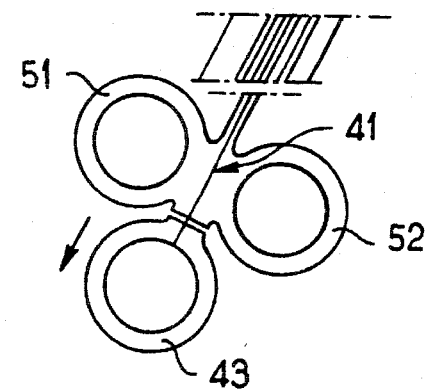
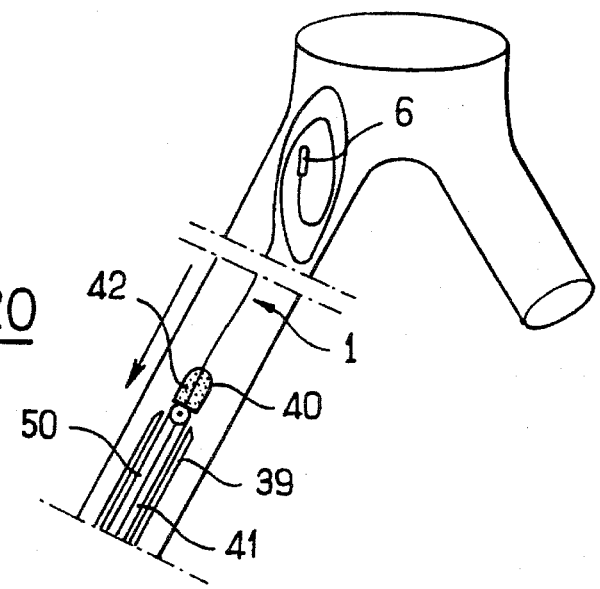
FIG_20

ANTI-PULMONARY EMBOLISM FILTER

This application is a continuation of U.S. application Ser. No. 07/844,617 filed Apr. 9, 1992 abandoned.

The present invention relates to an anti-pulmonary embolism filter and to a kit for presenting and installing the filter.

Various types of filter are already known and are actually in use for the purpose of being installed in the inferior vena cava in order to prevent clots migrating to the right heart from the veins of the lower limbs or of the true pelvis.

Particular mention may be made of the filters known under the names of: Mobin-Uddin, Greenfield, Gunther, and L.G. Medical.

All of these types of filter have in common structures that are substantially bodies of revolution (being cylindrical or conical) that must be folded up inside a sheath which is then pushed along the lumen of a catheter towards the implanting zone. Their insertion sheaths are of diameter equal to or greater than 3 mm and require large-caliber veins such as the internal jugular vein or the femoral vein.

Once installed in the inferior vena cava, these filters are released from their sheaths and their structures deploy themselves and enlarge the section of the vena cava moderately. They are bulky, difficult to install, and sometimes traumatic for the tissues of the vena cava against which they anchor themselves at several anchor points. It is not exceptional for such filters to be badly positioned or for them to migrate.

Another type of filter has been proposed in Document FR-A-2 541 901. In that document, the filter is made by means of a resilient wire shaped to have permanent successive undulations in different planes. Advantage is then taken of the resilience of the wire to straighten it out temporarily inside a catheter, and to convey it in this way to the implantation zone. On arrival in this zone, it is expelled from the catheter and is thereby released to take up its initial undulating shape so as to bear against the walls of the vena cava in a plurality of points in the various above-mentioned planes.

That proposal nevertheless has not given rise to practical implementations that are medically acceptable and it has therefore been abandoned.

Another type of filter is proposed in Document EP-A-0 323 333.

In that document, the filter is constituted by a resilient metal wire having a spring effect. Its special geometrical shape determines two loops in the form of perpendicular-axis ellipses that are of equal size and are coplanar, thereby giving four permanent points of contact with the wall of the vena cava in which it is implanted.

That type of filter has indeed been manufactured and experimented on animals and then on man. However, the medical difficulties that arise are so great both with respect to the filter-installation procedure and with respect to its mode of operation once installed, that generalized use of that filter cannot be recommended medically.

More precisely, a first difficulty resides in that the filter whose shape is initially as mentioned above, i.e. two ellipses with perpendicular axes, runs the risk, after being installed while temporarily rectilinear inside an installation catheter, of failing to return to its initial shape after being released from the catheter inside the inferior vena cava. This drawback gives rise to quite long quasi-rectilinear portions interconnecting the quasi-circular portions of the elongated quasi-ellipses. As a result there are unacceptable risks of the filter taking up the form of an elongate S-shape or of an 8-shape instead of being in the form of crossed ellipses. It no longer bears against the walls of the vena cava at four balanced points and as a result the vein is not flattened sufficiently so the filter can migrate, moving along the vein after it has been installed.

In addition, the planes of the ellipses are quasi-coplanar and the filter effect is guaranteed only if firstly the four points at which the filter bears against the wall of the vena cava are properly positioned, which cannot be guaranteed, as mentioned above, and if secondly the vena cava is very greatly flattened in order to reduce the cross-section of the vein very considerably, thereby obtaining the filter effect.

Finally, one end of the filter is fitted with a sharp point that slopes relative to the plane of the ellipses and that serves as an anchor point in the vena cava. This sharp point has two drawbacks: firstly it is difficult to insert into the catheter, and secondly there is a risk of traumatizing or even of perforating the wall of the vein.

An object of the present invention is to eliminate the drawbacks of prior filters, and subsidiarily to propose a new presentation and installation kit.

Throughout the remainder of this text, the adjective "proximal" is used in the common medical convention to indicate that portion of any item inserted into the blood circulation system which is closer to the point in the system to which the item needs to be taken, and the adjective "distal" is used to designate the portion of said item which is further away therefrom.

The anti-pulmonary embolism filter of the present invention is made from a spiral shaped resilient wire having a remanent spring effect, and it is characterized in that the spiral comprises three substantially circular non-touching turns with the middle turn having a diameter greater than the diameters of the other two turns, said diameter being selected to be close to one-half the circumference of the vena cava in the zone where the filter is to be implanted in order to ensure that the filter is optimally held in place by flattening of the vena cava.

This shaping of the filter into a spiral having three non-touching turns which constitutes the main characteristic of the invention has the essential advantage that on being released from the catheter inside which it is conveyed in a temporary rectilinear shape, the filter returns quite naturally to its initial shape since the filter comprises only curvilinear portions of substantially the same curvature.

Secondly, since the greater radius of the second turn is chosen to be close to the half-circumference of the vena cava, the function of holding the filter in place inside the vena cava is essentially performed by this middle turn since it bears strongly against the wall of said vena cava along opposite segments that extend practically over one-fourth of a circle each. Correct filter installation followed by stable positioning of the filter are thus obtained with certainty and safely by the vena cava being flattened. In addition, this flattening of the vena cava also enhances the filtering function since the section of the vena cava through which the blood flows is thus considerably reduced. The other two turns of the spiral having non-touching turns, turns which are therefore not coplanar with the middle turn, then optimally complement said filtering function in the vena cava since the blood flow passing through the filter thus encounters six semi-circular threadlike elements on its path.

According to another characteristic, the proximal end of the filter is provided with a radio-opaque ovoid element and the distal end of the filter is provided with a small radio-opaque cylinder having a rounded free end.

As described below in greater detail, these ends and radio-opaque elements make it possible to monitor the transfer of the filter to its implantation zone and then to monitor proper positioning thereof by means of X-rays. The ovoid element may optionally be used for subsequent removal of the filter if so desired.

According to another characteristic, the assembly comprising the filter wire and its ends shaped as specified above is coated with a thin layer of gold, firstly to prevent any corrosion phenomenon, and secondly to guarantee biocompatibility for the filter when installed inside a vena cava.

In addition, the spiral configuration of the filter, i.e. a configuration with curvature at all points, makes it possible to design a kit for presenting and installing the filter which is particularly adapted to the conditions of use of the filter in medical surroundings.

The present invention thus also provides such a kit of the type comprising:

a catheter; and a pusher constituted by a rigid endpiece having a longitudinal notch at its rounded proximal end for receiving the distal end of the resilient wire of the filter, followed by a housing for receiving the small distal cylinder of the filter, the rigid endpiece being secured at its distal end to a cable;

the kit being characterized by the fact that:

the catheter is terminated at its distal end by an endpiece provided with rapid coupling means;

the cable fixed to the distal end of the rigid endpiece is of length not less than the sum of the length of the catheter plus the length of the filter; and the kit being characterized by that the fact that it further comprises:

a transparent resilient tube having the same spiral configuration as the filter, the length of the tube being not less than the length of the filter and the tube serving as a storage and presentation container for the filter, said tube being fitted at its proximal end with first rapid coupling means for co-operating with the above-mentioned rapid coupling means of the catheter; and clamping means including a container suitable for receiving the pusher and provided at the distal end of the filter.

In a first variant embodiment, the clamping means comprise a rigid cylindrical housing constituted by two identical half-cylinders connected together by means of a hinge and intended to receive the assembly of the distal end of the filter as received in the housing of the rigid endpiece, the proximal end of said housing being provided with rapid coupling means cooperating with second rapid coupling means provided at the distal end of the tube.

The rigid housing forming a portion of the kit serves to assemble the distal end of the filter and the associated pusher just at the distal end of the filter storage tube. Thereafter, when the pusher is actuated the assembly (i.e. the pusher and the distal end of the filter) leaves the housing and enters initially into the transparent resilient tube, and then into the catheter, and it is thus maintained in the assembled state until it leaves via the proximal end of the catheter.

As a result, the last turn of the filter is released as soon as it leaves the catheter, which means that the position of the proximal end of the catheter inside the inferior vena cava must be monitored very accurately and this can sometimes be difficult.

In a second variant, the clamping means are constituted by a sheath including a flexible tubular first portion of internal caliber and of length adapted to enable the pusher cable to be guided therein and to slide freely therealong, and a rigid second portion in the form of a cylindrical tubular bell suitable firstly for receiving the distal end of the filter manually disposed in the pusher having the rigid endpiece, and secondly for being manually engaged in the distal end of the transparent resilient tube, the maximum outside diameter of the sheath being slightly less than the inside diameter of the catheter, and means being provided to selectively prevent the pusher from leaving the end of the sheath.

This second variant makes it possible to assemble and then disassemble the filter and the pusher with greater ease and with greater accuracy.

The second variant enables the entire sheath containing the pusher cable coupled to the filter to move forwards inside the catheter and then inside the lumen of the vena cava without them coming apart.

As a result the filter is installed in the vena cava in two stages: during the first stage, the proximal end of the catheter is installed in the selected region of the vena cava under X-ray monitoring making use of its radio-opaque marks, and to a sufficient first approximation; thereafter, during a second stage, the proximal radio-opaque end of the above-mentioned sheath is installed in a very accurate position in the vena cava. The cable is then allowed to move forwards inside the sheath and additional thrust of the pusher cable inside the sheath enables the distal end of the filter to be released, thereby completing filter installation.

According to another additional characteristic of the kit in compliance with either of the variant embodiments proposed above, the proximal end of the catheter is provided with two spaced-apart rings that are more radio-opaque than the catheter and that enable the diameter of the vena cava to be measured in the region where the filter is to be installed so as to make it possible to select the value to be given to the diameter of the middle turn accordingly.

The present invention also enlarges the kit by including means therein making it possible at any instant to recover the filter after it has been completely released inside the lumen of the inferior vena cava.

It may become necessary to be able to recover the filter after it has been installed, even after it has been properly installed, for medical reasons that have nothing to do with possible faulty installation of the filter nor with its effectiveness.

For example, it may be appropriate to recover the filter some time after it has been .installed once it has performed its anti-embolism function and after the risk of pulmonary embolism has disappeared. This may happen with young victims of road accidents who may initially present such risks.

To this end, the invention proposes adding a filter recovery hook guide to the above-mentioned kit characterized in that it is constituted by a flexible guide capable of sliding freely inside a catheter and is terminated by a rigid hook on the axis of the guide and having the form of a hairpin.

To recover a filter, the proximal end of the catheter housing the flexible hook guide is moved into the vena cava where the filter to be recovered has been implanted, and into the vicinity of the filter. By pushing the guide, the hook is caused to leave the end of the catheter and it is pushed until it goes past the filter. During a reverse movement, the hook catches one or more of the turns, and because of the resilience of the filter, steady traction causes the filter to deform and enter into the catheter ready for being removed.

In a particular embodiment, the free branch of the rigid hook is terminated by a flexible end sloping outwards from the hook so as to provide a flared opening to the hook for the purpose of catching the maximum number of turns of the filter to be withdrawn.

In a variant, the filter withdrawal means may be constituted by a withdrawal grab having two hinged jaws at one end, which jaws are rounded, radio-opaque, and hollow, and are suitable for being opened or closed, e.g. under control of a cable, so as to be able to capture and pull one end of the filter.

While in the open position, one or other of the ends of an installed filter that is to be withdrawn can be surrounded. The jaws are then closed to enable the filter to be withdrawn by traction, the filter being conveyed on its return journey into a withdrawal catheter.

The following description of particular embodiments of the means of the invention will further improve understanding of the advantageous characteristics thereof.

This description is given with reference to the accompanying drawings, in which:

FIG. 1 is a perspective view of a spiral filter having three non-touching turns together with its proximal and distal ends;

FIG. 2 is a plan view of the filter as it would appear when laid flat on a horizontal surface;

FIG. 3 is a diagrammatic side view of the filter clearly showing the special geometrical shape characteristics of the turns of the filter;

FIG. 4 shows the temporary rectilinear shape of the filter when inside a catheter;

FIGS. 5 and 6 show how a filter is transferred and released in position within a vena cava;

FIGS. 7 and 8 are respectively a cross-section of the vena cava and a longitudinal side view thereof showing the shape taken up by the spiral filter when in position in a vena cava;

FIG. 12 shows the second variant embodiment of such a kit;

FIG. 13 shows a hook guide for withdrawing the filter of the invention;

FIGS. 14 to 18 show the hook guide is used and how it operates; and

FIGS. 19 and 20 show a withdrawal grab of the invention and how it operates.

Figure 9:
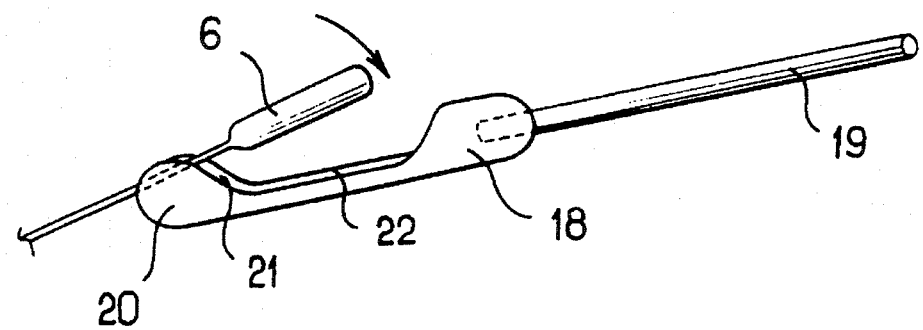
FIG. 9 shows a pusher for moving the filter forwards inside a catheter.

The following description relates successively to:

1) the characteristics of the wire and of the catheter for use in shaping a filter of the invention;

2) the shape of the filter itself and of its ends, and the effects of installing the filter in a vena cava;

3) the structure and the utilization of two variant kits for storing, presenting, and utilization of the filter; and 4) means for withdrawing the filter.

1. CHARACTERISTICS OF THE WIRE AND OF THE CATHETER

The anti-pulmonary embolism filter is made of a resilient wire, and most preferably of a metal wire. The filter must be non-magnetizable so as to make it possible for a patient with such a filter to be subjected to NMR or to MRI (magnetic resonance imaging) without damage. The wire must also be radio-opaque so as to be visible in X-ray examination.

The wire may be made of any suitable resilient material known to the person skilled in the art.

By way of non-limiting example, the wire may be made of an alloy selected from the group comprising the following alloys: 1) copper, nickel, and aluminum; 2) copper, zinc, and aluminum; 3) copper, zinc, aluminum, and nickel; and 4) copper, tin, and nickel.

A final coating of a thin layer of biocompatible material (preferably gold) is provided in order to avoid corrosion phenomena and to ensure biocompatibility.

The resilient wire is suitable for being shaped to a desired geometrical shape by mechanical and thermal treatment using techniques known in the technology of metal wires having permanent spring characteristics.

The diameter of the wire preferably lies in the range 0.25 mm to 1 mm, and is typically about 0.37 mm in order to enable it to be inserted in a 6F catheter. The size F (French) is 0.33 mm. A 6F catheter therefore has an outside diameter of 1.98 mm and its useful internal bore has a diameter of the order of 1.45 mm. A 6F catheter cannot be used for installing conventional filters that are at present in use since their diameter is too large, and they can be installed only via veins of large section, such as the femoral veins or the jugular veins. In contrast, in the context of the invention, filters are made suitable for moving inside a small diameter 6F catheter, thereby making it possible to install such filters via small veins. It is possible, for example, to start from one of the veins on the inside of the elbow.

The length of the wire constituting the filter lies preferably in the range 22 cm to 35 cm, depending on the size of the filter which is adapted, as explained below, to the bore size of the inferior vena cava of the patient.

The resilient quality of the wire used and its small diameter make it possible both for it to be made quasi-rectilinear under the effect of a small traction force for insertion inside a small diameter catheter, and for it to move therein in either direction without constraint, as shown in FIG. 4.

2. SHAPE OF THE FILTER AND OF ITS ENDS, AND THE FUNCTIONS THEREOF

Reference is made to FIGS. 1, 2, and 3.

According to the main characteristic of the invention, the filter 1 is shaped as a spiral having three non-touching turns 2, 3, and 4, the middle turn 3 having a diameter d3 which is greater than the diameters d2 and d4 of the other two turns 2 and 4. For the purpose of clarifying the geometrical shape of the filter, FIGS. 1, 2, and 3 show two small transversely-extending lines referenced T at the points where the turns 2, 3, and 4 run into one another.

As can be seen clearly in FIGS. 2 and 3, the turns 2, 3, and 4 are more or less coaxial and the diameters d2 and d4 may be equal, for example, but this condition is not critical. The turns 2, 3, and 4 are substantially centered on a common axis 7 normal to the plane of FIG. 2. The essential point is that the diameter d3 of the middle turn 3 is greater than the diameters d2 and d4 of the end turns 2 and 4.

The diameter d3 of the middle turn 3 is preferably $\geq 1.25$ d2 or d4, and most advantageously, $d3 \geq 1.42$ d2 or d4. The three turns 2, 3, and 4 are preferably at substantially identical pitch p.

While at rest and prior to being implanted, the pitch p of the spiral in FIG. 3 is not less than about 3 mm such that the total axial extent of the spiral at rest is not less than about 10 mm, regardless of the value of the diameter d3 of the middle or largest turn 3.

According to another advantageous characteristic of the present invention, to enable the filter to be installed properly, the diameter d3 of the middle turn 3 is greater than twice, and is typically >2.5 times the axial extent 3p of the filter at rest.

The size of the filter 1 must be adapted to the vena cava in which it is to be fitted. The size of the filter corresponds to the diameter d3 of the middle or largest turn 3. This size should be as close as possible to the half-circumference of the inferior vena cava as calculated from its diameter measured as described below. Thus, the turn of diameter d3 is always greater in diameter than the vena cava (FIGS. 5, 6, and 7) to obtain the best flattening effect of the vena cava by the installed filter. In practice, a size 1 can be selected of diameter d3 equal to 27 mm for venae cavae of diameter 16 mm to 18 mm, a size 2 of diameter d3 equal to 31.5 mm for venae cavae of diameters 19 mm to 21 mm, and a size 3 of diameter d3 equal to 36 mm for venae cavae of diameters greater than 22 mm.

The ends of the filter, like the wire, are opaque to X-rays so as to be clearly visible under luminance amplifiers.

The proximal first end 5 shown in FIGS. 1 to 4 is droplet or ovoid in shape, being rounded at its free end and tapering towards its end attached to the filter wire. This shape makes it possible for it to move in both directions inside the lumen of the catheter without damage and without constraint. Once it has left the catheter, the end 5 is the first part to come into contact with the smooth wall of the inferior vena cava. Its rounded shape avoids damaging the wall of the vein in any way and it enables it to slide over said wall so that the loops of the turns 2, 3, and 4 constituting the filter can coil up without constraint (FIGS. 5 and 6). In addition, the water-drop shape 5 makes it easy during a withdrawal operation to reinsert the filter inside a carrier catheter without blocking in the inlet orifice of the catheter. By way of non-limiting example, the dimensions of this ovoid proximal end 5 of the filter are about 1.3 mm at its largest diameter and 0.6 mm at its diameter where it joins the wire forming the filter 1. It may be about 3.5 mm long.

The distal second end 6 of the filter (FIGS. 1 to 3) is in the form of a small radio-opaque cylinder. By way of non-limiting example, the outside diameter of the cylinder 6 may be about 0.6 mm and its length may be about 4 mm. It is connected to the distal end of the filter wire. Its free end is smooth, and slightly rounded so as to avoid damaging the wall of the vena cava once it is in place.

The shape of the filter together with its ends defines the qualities thereof: for installation in the vena cava; for stability and remaining properly in position; and for its function of effectively filtering clots conveyed in the venous circulation.

The first turn 2 (FIGS. 1 to 6) which coils up first in the vena cava when the filter is pushed out from the catheter is smaller in diameter than the middle turn 3, thereby facilitating said first coiling up.

Coiling up continues with the middle turn 3. Its diameter d3 which is greater than that of the vein in which it is implanted deforms the vena cava by flattening it heightwise, i.e. in the circulation direction of the blood flow. This flattening effect results in a considerable reduction in the through section available for the blood flow in the vena cava, as can be seen in FIGS. 7 and 8.

The third turn 4 has a diameter of the same order as the first turn 2. It coils up last, and on leaving the catheter it releases its distal end 6 automatically by the spring effect.

The fact that the spiral presents substantially continuous and uniform curvature over its entire length guarantees that its shape on entering the catheter and then on leaving it is maintained in spite of it being temporarily deformed into a rectilinear shape while being transferred inside the catheter. In addition, the high pressure exerted by the circular arcs of the turns in contact with the vein wall, and essentially by the arcs of the middle turn, guarantees that the filter is held in place without any risk of it migrating.

As can be seen more particularly in FIGS. 7 and 8, the thickness of the filter due to the pitch p of its three turns enables the filter to stop clots that are small in size, e.g. of the order of 3 mm. They tangle with the loops of the filter which constitute a grid in the flattened lumen of the vein.

The resulting filtering is due to two combined effects: firstly the flattening of the vena cava in the implantation zone; and secondly the presence of various arcs of the filter across the vena cava.

It turns out that a spiral having three turns is optimal for obtaining a filtering effect. A larger number of turns would pointlessly increase the length of the wire when uncoiled.

This would increase the difficulty of transferring it via a catheter.

A smaller number of turns would reduce the filtering effect.

However, the definition of the invention should not be limited specifically to a three-turn geometrical shape. It is clear that a filter having a number of turns that is slightly greater or slightly less than three would still be satisfactory.

The shape of the filter which is not traumatic for the vein avoids any portion of the filter penetrating into the wall of the vein. After being implanted, the spiral arcs in contact with the wall of the vein are progressively covered with endothelial tissue. The time required for the filter to become definitively fixed in a vein is not less than about 14 days such that during this time interval it is still possible to withdraw it percutaneously, i.e. without performing a surgical operation.

3. KITS FOR STORAGE, PRESENTATION, AND UTILIZATION OF A FILTER

Figure 10:
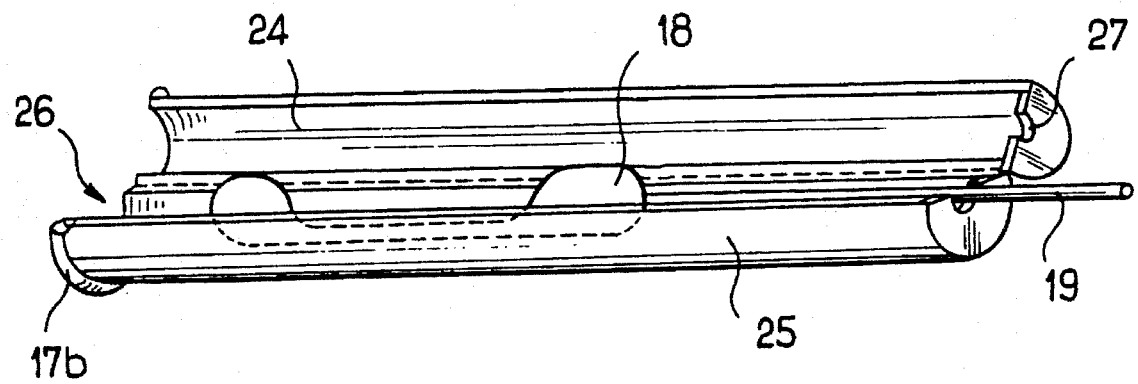
FIG. 10 shows a housing enabling the filter and the pusher to be assembled together.
Figure 11:
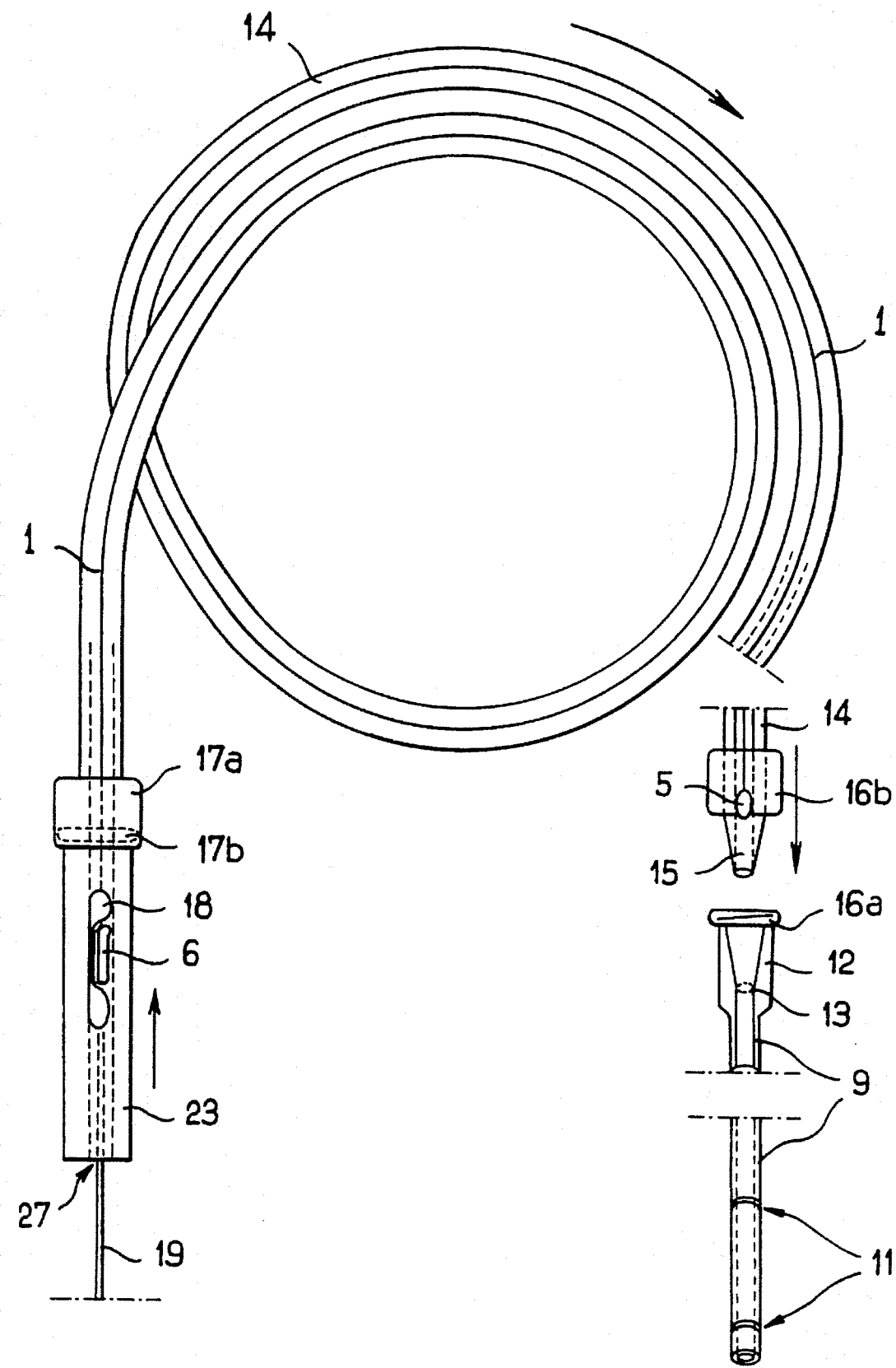
FIG. 11 shows an assembled assembly of the four components of a kit for storing, presenting, and using a filter of the invention and in accordance with the first above-mentioned variant.

Preference is now made to FIGS. 9 to 11 while describing a first variant embodiment of a kit adapted to the filter of the invention for ensuring optimum storage, presentation, and implementation in medical surroundings.

The kit comprises firstly a catheter 9 which is preferably selected to be of 6F caliber for the reasons explained above. It may be made, for example, of flexible and radio-opaque polyethylene. It must be at least one meter long.

Its proximal end, i.e. the first end to be inserted in the vein, has two narrow rings 11 fixed on its outside and more radio-opaque than the catheter itself, which rings are 20 mm apart (FIGS. 11 and 12). Their function is to make it possible to measure the magnification factor required for correcting distances as altered by the distortion due to X-rays. It is thus possible to determine which size (1, 2, or 3, see above) of filter is suitable for the measured diameter of the vena cava of a patient being treated.

The distal end of the catheter includes a rigid endpiece 12 having a screw thread 16a to international standards. Its orifice is conical being flared toward its inlet. It tapers to the diameter of the lumen of the catheter which it runs into via a section 13.

Secondly, the kit includes a resilient transparent tube 14 having the same spiral shape with non-touching turns as the filter 1. Having a length that is not less than that of the filter, and serving as a container for storing the filter, for presenting it, and for using it.

Prior to use, inside the packaging of the kit, the catheter 9 is on its own as are the other parts of the kit. The container tube 14 contains the filter 1 with its proximal ovoid end 5 being inside the container 14 and with its distal small cylinder end 6 projecting from the distal end of the container tube 14. The filter 1 is thus stored while it is in its spiral shape having three non-touching turns.

The inside caliber of the tube 14 is exactly the same as that of a 6F catheter, i.e. 1.45 mm, thereby enabling the filter to be moved therealong without constraint by means of its end 5 and an endpiece pusher described below.

The proximal first end of the tube 14 is secured to the distal end of the catheter 9 via a moving nut 16b situated in front of the tapering end of the tube 14. This nut 16b matches the screw thread of the rigid endpiece 12 on the catheter 9.

At the other end of the tube 14 there is a second nut 17a that can move along its axis.

Thirdly, the kit includes a pusher shown in FIG. 9. This pusher is constituted by a rigid endpiece 18 which is secured coaxially to the end of a braided flexible steel cable 19, e.g. having a diameter of 0.7 mm and a length corresponding to not less than the sum of the length of the catheter and the length of the filter.

The rigid endpiece 18 is typically 10 mm to 12 mm long, rectilinear, cylindrical, and 1.3 mm in diameter, is matched to the inside caliber of the 6F catheter 9 so as to be to slide therein without friction, and has a free end 20 which is blunt, rounded, hemispherical, and non-traumatic for the catheter and the vein. This rounded end includes a first lateral notch 21 in its lengthwise direction designed to receive the filter wire 1. This notch 21 is followed by a recess 22 of length 5 mm to 6 mm designed to receive the small distal cylinder 6 of the filter.

Fourthly, and finally, the kit includes a housing for assembling the filter to the pusher, as shown in FIG. 10.

The housing is constituted by a cylindrical rigid plastic tube comprising two same-diameter half-cylinders 24 and 25. The half-cylinders 24 and 25 are joined together by a moving flexible hinge made of plastic. Initially, this tube remains in the open position. It is about 30 mm to 35 mm long. Its outside diameter is designed so that a screw thread 17b disposed at a first one of its ends 26 can be screwed into the moving nut 17a (FIG. 11) when the housing is closed. In this state, the two end orifices 26 and 27 in the proximal face and in the distal face respectively, are of different calibers.

The proximal first orifice 26 with the screw thread 17b around the periphery thereof has a diameter that is exactly identical to the inside caliber of the flexible tube 14 of the 6F catheter, i.e. 1.45 mm.

The endpiece 18 of the pusher containing the distal cylinder 6 of the filter 1 (FIG. 11) can slide via this orifice 26 inside the tube 14 when the housing 23 is screwed thereon.

The distal second orifice 27 (FIGS. 10 and 11) has a caliber that is slightly greater than that of the cable 14 of the pusher 18, but less than that of the orifice 26, so as to prevent the endpiece 18 of the pusher escaping from the rigid box 23 when it is closed.

The two half-cylinders 24 and 25 are identical. In the closed position, the inside diameter is the same as that of the tube 14, i.e. 1.45 mm. The function of this rigid housing is to enable the end 6 of the filter 1 to be easily secured in the recess 22 of the pusher 18. When the cylinder 6 is placed in the recess 22, it suffices to close the rigid housing 23 and then to screw the screw thread 17b at its first end to the coupling 17a of the tube 14 so that the filter becomes secured to the pusher 18 by means of the cylinder 6. Thereafter, the filter 1 can be moved to the proximal end of the catheter 9 and can be released inside the vena cava merely by pushing on the cable 19. Once all three circular turns of the filter 1 have taken up their shape inside the vena cava, the distal end 6 is released by pushing the endpiece of the pusher 18 into the lumen of the vein. Automatically by the spring effect the end 6 escapes from the housing 22 of the endpiece 18. However, if there should be difficulty in releasing the filter, it is still possible to withdraw the entire filter 1 and the pusher 18 by pulling on the pusher cable 19. After withdrawal, the rigid housing 23 merely requires unscrewing from the tube 14. The housing then opens automatically and the end 6 of the filter escapes automatically from the housing 22 of the pusher 18 by virtue of its spring effect.

A second variant of the kit is shown in FIG. 12. In this figure, the same reference numerals as those used in FIG. 11 mark items that are identical. FIG. 12 includes a catheter 9, a tube 14, a filter 1, and a pusher 18 fitted with a cable 19.

The distal end of the tube 14 is shaped as a tapering female endpiece 30.

The kit of FIG. 12 does not include a housing 23, but instead has a sheath including a flexible tubular first portion 31 of internal caliber and of length selected so that the pusher cable 19 can be guided therein and can slide freely therein.

The outside diameter of the sheath is less than or equal to the caliber of the tube 14 and of the catheter 9.

The sheath includes a rigid proximal second portion in the form of a cylindrical tubular bell 32. This bell receives the distal end of the filter 6 which is housed manually in the housing 22 of the pusher having a rigid endpiece 18. Once this has been achieved, the sheath 31 is prevented from being withdrawn over the cable 19 of the pusher by a split nut means 33 and by a lock nut 34 which fasten on the cable 19 and which are placed adjacent to the distal end of the sheath to serve as an abutment therefor.

Thereafter, when the filter is installed, it is very easy to insert the bell 32 into the female end 30 of the transparent tube.

To release the end 6 of the filter, it is necessary to disconnect the part 18 of the pusher at the desired moment from the spring effect resilient end 6 of the filter. In the venous flow outside the lumen of the catheter, the bell 32 at the proximal end of the flexible sheath 31 covers the fastened-together pusher 18 and end 6. After the nuts 33 and 34 have been loosened, merely applying traction from the flexible sheath on the pusher serves to uncover the part 18 from which the end 6 of the filter escapes automatically. It is thus possible to check that all three spiral turns forming the filter 1 have indeed taken up the proper shape before releasing the end of the filter.

4. MEANS FOR WITHDRAWING THE FILTER

The description now relates to a hook guide making it possible to retrieve the filter at any moment. The hook guide is as shown in FIGS. 13 to 18. It is associated with a catheter 9 similar to that described above. The guide 34 is flexible and can take up any of the curvatures imposed by the catheter without presenting difficulties in moving therealong. The guide is made of biocompatible, non-thrombosisgenerating steel alloy which is covered in polytetrafluoroethylene (known commercially under the trademark Teflon). It is opaque to X-rays. It is recalled that the inside diameter of a 6F catheter is 1.45 mm.

The hook 35 is situated at the head of the guide lying on the axis thereof. It is curved at the end to give it a hairpin shape. The hook 35 is rigid. It is radio-opaque and made of steel. Its diameter is less than that of the guide itself, e.g. by 0.4 mm, and it is about 12 mm long. The resulting loop thus leaves a large amount of space between the two branches 36 and 37 that form the hook 35.

The free end 38 of the branch 37 of the hook 35 extends outwards at an angle of 30° to 45°. This flagellate flexible end is 2 mm to 3 mm long. It is resilient. Thus, the hook is non-traumatic both for the wall of the inferior vena cava and for the carrying catheter. In addition, its rearwards flare makes it easier to hook onto one or more turns of a filter installed in the inferior vena cava as shown in FIG. 15.

Once the filter has been caught by the hook 35 of the recovery guide 34, it can be withdrawn into the lumen of the catheter 9 as shown in FIG. 17.

The flexible end 38 terminating the hook makes it possible to close the hook either by holding it exactly against the proximal orifice of the catheter 9 (FIG. 16) or else by bringing it into the catheter (FIG. 17).

The hooked turn(s) can no longer escape from the hook 35. The entire filter is moved along the lumen of the inferior vena cava by traction (FIG. 18). The flexibility of the filter and its resilience enable it to fold so as to be withdrawn in full or in part inside the catheter 9.

The assembly constituted by the carrying catheter 9, the hook recovery guide 34, and the filter 1 is withdrawn to the inlet orifice to the vein whereby these parts were inserted into the body, with the filter folded onto itself taking up the inside diameter of the vein along which it is moved. This recovery of the filter by hooking it can be performed in any direction of movement of the 6F catheter in the vena cava. Thus, it is possible to approach via the femoral vein or via the internal jugular vein in the neck.

The withdrawal operation can also be performed by means of a more elaborate tool as shown in FIGS. 19 and 20. This "grab" withdrawal tool essentially comprises an elongate support body 50 suitable for being engaged inside catheter 39 and provided with two finger rings 51 and 52 at its distal end and with two rounded hollow radio-opaque jaws 40 and 42 suitable for being opened and closed and which are hinged to the proximal end of the support 50 about an axis 53. The jaws 40 and 42 are preferably resiliently urged towards an open position.

They may be closed by applying traction (or thrust) on a cable 41 which runs along the support 50 and which terminates at a finger ring 43 that is accessible at the distal end of the support 50. The resilient member urging the jaws towards the open position is not shown in FIGS. 19 to 20 in order to simplify the drawing.

When open, the grab can catch one of the two ends 5 or 6 of the filter (FIG. 19). The grab is then closed under control of the cable 41 and then merely by applying traction the filter winds out from the vein and follows the path of the grab which is withdrawn along the rigid catheter 39 as shown diagrammatically in FIG. 20.

Various lengths of withdrawal grab are possible in the range 50 cm to 1 m. It constitutes a flexible tool having an outside diameter adapted to move inside a rigid carrier catheter 39 of a caliber greater than that used for installing the filter. The catheter 39 is likewise inserted percutaneously.

The entire tool is shaped so as to avoid being traumatizing. The jaws cannot damage the wall of the vein.

The withdrawal operation may be performed from the jugular vein or from the femoral vein.

Naturally, the above description of particular embodiments of the invention is given purely by way of example. Numerous variants, embodiments, and/or different sizes may be imagined without thereby going beyond the ambit of the invention as defined in the following claims.

We claim:

1. An anti-embolism filter for implanting in a vena cava comprising a rectilinear resilient wire having a remanent spring effect shaped into a spiral structure comprising three substantially circular non-touching coaxial turns formed of a middle turn and two lateral turns, with the two lateral turns having at least substantially equal diameters, while the middle turn has a diameter greater than the diameter of each of the two lateral turns, said diameter of the middle turn being greater than 16 mm so as to be about one-half a circumference of the vena cava in a zone where the filter is to be implanted in order to ensure that the filter is optimally held in place by flattening of the vena cava when said filter is implanted in said vena cava with its axis perpendicular to the axis of said vena cava, wherein each of a proximal end and a distal end of the filter are provided with a radio-opaque element and, when implanted in the vena cava, the filter retains any clot migrating with the blood before said clot penetrates into the heart to avoid pulmonary embolism while allowing free flowing of the fluid blood in the vena cava.

2. An anti-embolism filter for implanting in a vena cava comprising a rectilinear resilient metal wire having a remanent spring effect shaped into a spiral structure comprising three substantially circular non-touching coaxial turns formed of a middle turn and two lateral turns, with the two lateral turns having at least substantially equal diameters, while the middle turn has a diameter greater than 16 mm and greater than 1.4 times the diameter of each of the two lateral turns, so that said diameter of the middle turn is about one-half a circumference of the vena cava in a zone where the filter is to be implanted with its axis perpendicular to the axis of said vena cava in order to ensure that the filter is optimally held in place by flattening of the vena cava, wherein, when implanted in the vena cava, the filter retains any clot migrating with the blood before said clot penetrates into the heart to avoid pulmonary embolisms while allowing free flowing of the fluid blood in the vena cava, and wherein the pitches of the three turns are substantially equal and each of a proximal end and a distal end of the filter are provided with a radio-opaque element.

3. An anti-embolism filter for implanting in a vena cava comprising a rectilinear resilient wire having a remanent spring effect shaped into a spiral structure comprising three substantially circular non-touching turns with a middle turn adjacent two end and having a diameter greater than a diameter of each of the two end turns, said diameter of the middle turn being greater than 16 mm so as to be about one-half of the vena cava circumference where the filter is to be implanted with its axis perpendicular to the axis of said vena cava in order to ensure that the filter is optimally held in place by flattening of the vena cava, wherein, when implanted in the vena cava, the filter retains any clot migrating with the blood before said clot penetrates into the heart to avoid pulmonary embolism while allowing free flowing of the fluid blood in the vena cava.

4. An anti-pulmonary embolism filter according to claim 3, characterized in that the filter has a proximal end provided with a radio-opaque ovoid element.

5. An anti-pulmonary embolism filter according to claim 3, characterized in that the filter has a distal end provided with a radio-opaque cylinder having a rounded free end.

6. An anti-pulmonary embolism filter according to claim 3, characterized in that it is made of metal.

7. An anti-pulmonary embolism filter according to claim 6, characterized in that it is made from an alloy selected from the group consisting of: 1) copper, nickel, and aluminum; 2) copper, zinc, and aluminum; 3) copper, zinc, aluminum, and nickel; and 4) copper, tin, and nickel.

8. An anti-pulmonary embolism filter according to claim 3, characterized in that the wire of the filter and its ends are covered overall with a thin layer of gold.

9. An anti-pulmonary embolism filter according to claim 3, characterized in that the two end turns are of substantially equal diameters.

10. An anti-pulmonary embolism filter according to claim 3, characterized in that the three turns are substantially coaxial.

11. An anti-pulmonary embolism filter according to claim 3, characterized in that wire has a diameter of 0.25 mm to 1 mm.

12. An anti-pulmonary embolism filter according to claim 11, characterized in that the filter has a diameter of 0.37 mm.

13. An anti-pulmonary embolism filter according to claim 3, characterized in that the filter has a total length of about 22 cm to 35 cm.

14. An anti-pulmonary embolism filter according to claim 3, characterized in that the diameter of the middle turn is at least 1.25 times the diameters of the end turns.

15. An anti-pulmonary embolism filter according to claim 3, characterized in that the diameter of the middle turn is at least 1.4 times the diameters of the end turns.

16. An anti-pulmonary embolism filter according to claim 3, characterized in that the three turns have substantially equal pitches.

17. An anti-pulmonary embolism filter according to claim 3, characterized in that the spiral, when at rest and prior to implantation, has a pitch of not less than 3 mm.

18. An anti-pulmonary embolism filter according to claim 3, characterized in that the filter, at rest prior to implantation, has an axial extent of at least 9 mm.

19. An anti-pulmonary embolism filter according to claim 3, characterized in that the diameter of the middle turn is at least 2 times the filter's axial extent when at rest prior to being implanted.

20. An anti-pulmonary embolism filter according to claim 4, characterized in that the ovoid element provided at the proximal end of the filter has a maximum diameter of about 1.3 mm and a maximum length of about 3.5 mm.

21. An anti-pulmonary embolism filter according to claim 5, characterized in that the radio-opaque cylinder has a diameter of about 0.6 mm and a length of about 4 mm.

22. An anti-embolism filter for implanting in a vena cava comprising a rectilinear resilient metal wire having a remanent spring effect shaped into a spiral structure comprising three substantially circular, non-touching coaxial turns in form of a middle turn and two lateral turns, with the two lateral turns having at least substantially equal diameters, while the middle turn has a diameter greater than 1.4 times the diameter of each of the two lateral turns, said diameter of the middle turn being greater than 16 mm so as to be about one-half the circumference of the vena cava in a zone where the filter is to be implanted with its axis perpendicular to the axis of said vena cava in order to ensure that the filter is optimally held in place by flattening of the vena cava, wherein the pitch of the three turns are substantially equal, the axial extent of the filter at rest prior to implantation is at least 9 mm, the diameter of the middle turn is greater than 2 times the axial extent at rest of the filter prior to being implanted and a proximal end and a distal end of the filter are provided with a rounded radio-opaque element, and wherein, when implemented in the vena cava, the filter retains so as to retain any clot migrating with the blood before said clot penetrates into the heart, to avoid pulmonary embolism, while allowing free flowing of the fluid blood in the vena cava.

23. An anti-embolism filter for implanting into the vena cava consisting of a rectilinear resilient wire having a remanent spring effect shaped into a spiral structure comprising three substantially circular non-touching coaxial turns with a middle turn adjacent two end turns and having a diameter greater than the diameter of each of the two end turns, said diameter of the middle turn being 27–36 mm so as to be about one-half of the vena cava circumference where the filter is to be implanted with its axis perpendicular to the axis of said vena cava in order to ensure that the filter is optimally held in place by flattening of the vena cava.

24. An anti-embolism filter for implanting into the vena cava consisting of a rectilinear resilient wire having a remanent spring effect shaped into a spiral structure consisting of three substantially circular non-touching coaxial turns with a middle turn adjacent two end turns and having a diameter greater than the diameter of each of the two end turns and greater than 16 mm, so as to be about one-half of the vena cava circumference where the filter is to be implanted with its axis perpendicular to the axis of said vena cava in order to ensure that the filter is optimally held in place by flattening of the vena cava.

25. An anti-embolism filter for implanting into a vena cava comprising a rectilinear resilient single wire having a remanent spring effect shaped into a spiral structure comprising three substantially circular non-touching coaxial consecutive turns with a middle turn adjacent two end turns and having a diameter greater than the diameter of each of the two end turns, said diameter of the middle turn being 27–36 mm so as to be about one-half of the vena cava circumference where the filter is to be implanted with its axis perpendicular to the axis of said vena cava in order to ensure that the filter is optimally held in place by flattening of the vena cava, wherein, when implanted in the vena cava, the filter retains any clot migrating with the blood before said clot penetrates into the heart to avoid pulmonary embolism while allowing free flowing of the fluid blood in the vena cava.

26. An anti-embolism filter for implanting into a vena cava comprising a rectilinear resilient single wire having a remanent spring effect shaped into a spiral structure consisting of three substantially circular non-touching coaxial consecutive turns with a middle turn adjacent to two end and having a diameter greater than the diameter of each of the two end turns and greater than 16 mm, so as to be about one-half of the vena cava circumference where the filter is to be implanted with its axis perpendicular to the axis of said vena cava in order to ensure that the filter is optimally held in place by flattening of the vena cava, wherein, when implanted in the vena cava, the filter retains any clot migrating with the blood before said clot penetrates into the heart to avoid pulmonary embolism while allowing free flowing of the fluid blood in the vena cava.

27. An anti-embolism filter for implanting into the vena cava made of a rectilinear resilient wire having a remanent spring effect shaped into a spiral structure comprising a non-planar spiral having two lateral turns connected by a middle turn having a diameter greater than the diameter of each of the lateral turns and greater than 16 mm, in order to assure that, when the filter is implanted in the vena cava with its axis perpendicular to the axis of said vena cava, the filter flattens the vena cava and is optimally held in place so as to retain any clot migrating with the blood before said clot penetrates in the heart to avoid pulmonary embolism while allowing free flowing of the fluid blood.

* * * * *